United States Patent [19]

Reifenberg

[11] 4,129,584
[45] Dec. 12, 1978

[54] PROCESS FOR PREPARING DIMETHYLTIN DICHLORIDE

[75] Inventor: Gerald H. Reifenberg, Hightstown, N.J.

[73] Assignee: Pennwalt Corporation, Philadelphia, Pa.

[21] Appl. No.: 828,578

[22] Filed: Aug. 29, 1977

[51] Int. Cl.$^2$ ............................................. C07F 7/22
[52] U.S. Cl. .................................................. 260/429.7
[58] Field of Search ....................................... 260/429.7

[56] References Cited

U.S. PATENT DOCUMENTS

| | | | |
|---|---|---|---|
| 3,387,011 | 6/1968 | Coates et al. | 260/429.7 |
| 3,415,857 | 12/1968 | Hoye | 260/429.7 |
| 3,519,665 | 7/1970 | Molt et al. | 260/429.7 |
| 3,857,868 | 12/1974 | Witman et al. | 260/429.7 |
| 3,901,824 | 8/1975 | Knezevic et al. | 260/429.7 X |

*Primary Examiner*—Helen M. S. Sneed
*Attorney, Agent, or Firm*—Robert G. Danehower

[57] ABSTRACT

A process is provided for preparing dimethyltin dichloride by the reaction of tin metal and methyl chloride in the presence of sulfonium or isothiuronium salts as catalysts.

12 Claims, No Drawings

PROCESS FOR PREPARING DIMETHYLTIN DICHLORIDE

BACKGROUND OF THE INVENTION

A number of catalytic processes have been developed for the preparation of dimethyltin dichloride by the reaction of tin metal with methyl chloride.

Hoye et. al. in U.S. Pat. No. 3,415,857 describes the use of onium salts as catalysts for the preparation of dialkyltin dihalides from tin metal and an alkyl halide. His catalyst system consists of a stannous or organotin chloride or bromide in addition to the onium salt in approximately equimolar amounts and optionally a metal other than tin. The reaction times are usually greater than 12 hours and yields range from moderate to poor. In fact, reasonable yields are only obtained when the catalyst residue is recycled as in Examples 10 and 11.

Molt et. al. in U.S. Pat. No. 3,519,665, discloses the use of tetraalkylphosphonium or tetraalkylammonium iodides as catalysts for the preparation of dialkyltin dichlorides from tin metal and an alkyl chloride. Because iodides are expensive, it becomes necessary to distill the product in order to recover the catalyst residues for re-use. Moreover, yields of dialkyltin dichlorides are generally poor.

Witman et. al. in U.S. Pat. No. 3,857,868, reported that quarternary ammonium salts are effective catalysts for preparing dimethyltin dichloride from tin metal and methyl chloride provided that the reaction is run under constant pressure, at least 60 psi, and in the presence of a solvent. To maintain constant pressure throughout the reaction, methyl chloride must be fed into the system periodically.

Knezevic et. al., in U.S. Pat. No. 3,901,824, discloses the use of a two-component catalyst system for the preparation of dimethyltin dichloride from tin metal and methyl chloride. The catalyst system consists of: (a) tin tetrachloride; and, (b) a trihydrocarbylamine, a trihydrocarbylphosphine, a tetraalkylammonium chloride, or a tetraalkylphosphonium chloride.

DETAILED DESCRIPTION OF THE INVENTION

I have now discovered that dimethyltin dichloride of high purity can be prepared in essentially quantitative yields and in relatively short periods of time by carrying out the direct methylation of metallic tin with methyl chloride in the presence of at least one sulfonium or isothiuronium salt as catalyst. The reaction is represented by equation 1.

$$\text{Sn} + 2\text{CH}_3\text{Cl} \xrightarrow{catalyst} (\text{CH}_3)_2\text{SnCl}_2 \quad (1)$$

An added advantage of the present invention is that a majority of the catalysts are relatively low in cost which makes recycling and recovery of the catalyst unnecessary. Since the dimethyltin dichloride is formed in both high purity and high yields a truly economic one-step process is provided.

My process for preparing dimethyltin dichloride can be carried out at either atmospheric or superatmospheric pressure, the latter being preferred. Reaction pressure may range from 0 to 1500 pounds per square inch gauge pressure.

The sulfonium and isothiuronium salt catalysts which are operable in this invention are described by the following formulas:

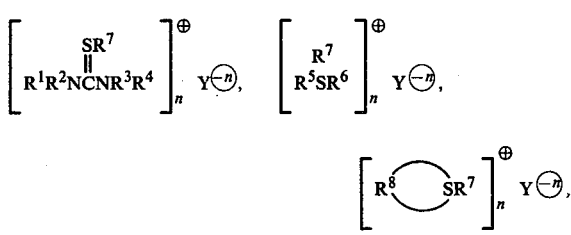

wherein: $R^1$, $R^2$, $R^3$, $R^4$, $R^5$, $R^6$, and $R^7$ are hydrocarbyl radicals including alkyl, aryl, aralkyl, alkaryl, or cycloalkyl of 1–24 carbon atoms. The hydrocarbyl radicals may be saturated or they may be unsaturated. They may also contain inert substituents such as ethers, esters, alcohols, halides, etc. $R^1$, $R^2$, $R^3$, and $R^4$ can also be hydrogen; $R^8$ is a hydrocarbon linking group of 3–5 carbon atoms. n is the valence of the anion Y; and Y is an anion including $Cl^{-1}$, $Br^{-1}$, $I^{-1}$, $SnCl_3^{-1}$, $SnBr_3^{-1}$, $SnI_3^{-1}$, $SnCl_5^{-1}$, $SnCl_6^{-2}$, $SnBr_5^{-1}$, $SnBr_6^{-2}$, $SnI_5^{-1}$, $SnI_6^{-2}$, and complexes formed by reacting $Cl^-$ or $Br^-$ with polyvalent metal halides such as $FeCl_2$, $FeCl_3$, $MgCl_2$, $CaCl_2$, $ZnCl_2$, $ZnBr_2$, $NiCl_2$, $CoCl_2$, $CuCl_2$, $PbCl_2$, $AlCl_3$, $TiCl_4$, $ZrCl_4$, etc. Generally, n will have a valence of 1 or 2.

Examples of suitable sulfonium and isothiuronium salt catalysts are trimethylsulfonium chloride, trimethylsulfonium bromide, trimethylsulfonium iodide, trimethylsulfonium trichlorostannite, triethylsulfonium iodide, tributylsulfonium bromide, tridodecylsulfonium chloride, tribenzylsulfonium iodide, triphenylsulfonium chloride, dimethylbutylsulfonium chloride, dimethyl-β-phenylpropylsulfonium iodide, dimethyl-o-ethylphenylsulfonium chloride, dimethylethylsulfonium bromide, dimethylbenzylsulfonium iodide, methylethylpropylsulfonium chloride, dimethylisopropylsulfonium tribromostannite, dimethyl t-butylsulfonium triiodostannite, methylethylcyclohexylsulfonium iodide, dibenzylallylsulfonium bromide, dimethyltolylsulfonium chloride, tetramethylenemethylsulfonium bromide, tetramethylenemethylsulfonium chloride, tetramethylenemethylsulfonium iodide, tetramethylenemethylsulfonium trichlorostannite, pentamethylenebutylsulfonium iodide, bis(trimethyl sulfonium)hexachlorostannate, trimethylsulfonium tetrachloroaluminate, trimethylsulfonium trichlorozincate, bis(tetramethylenemethylsulfonium) tetrachlorocuprate (II), tetramethylenemethylsulfonium hexachlorotitanate (IV), bis(tetramethylenemethylsulfonium) hexabromostannate, S-methylisothiuronium chloride, S-methylisothiuronium bromide, S-methylisothiuronium iodide, S-butylisothiuronium iodide, S-ethylisothiuronium iodide, S-t-butylisothiuronium chloride, bis(S-octylisothiuronium) hexachlorostannate, S-cyclohexylisothiuronium iodide, S-β-phenylethylisothiuronium trichlorostannite, N,N,N',N'-S-pentamethylisothiuronium iodide, N,N,N',N'-tetraphenyl-S-benzylisothiuronium chloride, N-ethyl-S-propylisothiuronium bromide, N,N'-diphenyl-S-2-ethylhexylisothiuronium iodide, N,N-dimethyl-N',N'-diethyl-S-butylisothiuronium chloride, N,N,N',N'-tetramethyl-S-isopropylisothiuronium iodide, S-methylisothiuronium pentachlorostannate, S-ethylisothiuronium tetrachloroferrate (III), S-butylisothiuronium trichloroplumbite, and bis(S-benzylisothiuronium) tetrachlorocobaltate (II).

Preferred catalysts are the chloride, bromide, and iodide salts of the trimethylsulfonium, tetramethylenemethylsulfonium, S-benzylisothiuronium, S-methylisothiuronium, S-ethylisothiuronium, and S-butylisothiuronium cations. The most preferred catalysts from a cost standpoint are trimethyl sulfonium chloride, and tetramethylenemethylsulfonium chloride. One or more catalysts can be employed in my process.

The isothiuronium and sulfonium salts of this invention need not be preformed and added as such but can be formed in situ by adding the appropriate reagents. Thus, if dimethylsulfide and an excess of methyl chloride are added to the reaction mixture, there is formed trimethylsulfonium chloride. Similarly, from thiourea and N,N,N',N'-tetrabutylthiourea, there is formed S-methylisothiuronium chloride and N,N,N',N'-tetrabutyl-S-methylisothiuronium chloride.

One or more catalysts can be employed in my process at the same time. The sulfonium catalysts can be prepared by reacting a hydrocarbyl halide as disclosed in "Organic Chemistry of Bivalent Sulfur", by Reid, Chemical Publishing Co., Inc., N.Y.C. 1960, Volume 2, pages 66 to 72.

The isothiuronium salts can be prepared by reacting thiourea with a hydrocarbyl halide as disclosed in "Organic Chemistry of Bivalent Sulfur", by Reid, Chemical Publishing Co., Inc., N.Y.C. 1960, Volume 5, pages 27 to 29.

The amount of catalyst employed in the preparation of dimethyltin dichloride may range from about 0.001 to 1.0 mole per g-atom of tin metal. As the amount of catalyst is increased, the reaction rate increases, provided that the temperature and the pressure of the reaction mixture are kept constant. Iodide salt catalysts of the same cation increase the reaction rate relative to the chloride or bromide salts provided that the temperature, pressure, and the amount of catalyst are kept constant. Preferably, the catalyst is employed in an amount of about 0.1 to 0.2 mole per g-atom of tin metal when the reaction is run atmospherically and about 0.001 to 0.10 mole per g-atom of tin metal when the reaction is run superatmospherically. The catalyst is placed in the reacton at the beginning of the reaction or it may be produced in the reaction as discussed above.

The reaction temperature should be within the range of about 120° C. to 300° C. Preferably, the reaction temperature will be within the range of about 130° C. to 220° C. Reaction time can vary from about 0.5 to 24 hours. Generally, the reaction time will vary within the range of about 1 to 8 hours. The time and temperature depend on the identity of the catalyst, the amount of catalyst, and whether the reaction is run atmospherically or superatmospherically. For example, the greater the amount of catalyst present within the desired range, the faster the reaction will proceed.

Any type of tin metal (mossy, granular, powder, or shot) may be used. In order for all of the tin metal to be consumed, at least 2 moles of methyl chloride are required per g-atom of tin. If the catalyst is formed in situ then an additional mole of methyl chloride is required for each mole of a dihydrocarbyl sulfide, thiourea, or substituted thiourea used. An excess (up to 50%) of methyl chloride has no adverse effect on the reaction and may, in fact, be beneficial. A methyl chloride excess greater than 50% is generally wasteful and provides no additional advantage. Both tin metal and methyl chloride are available in commercial quantities.

At least one solvent for methyl chloride is required at the beginning of the reaction, whether the reaction is run at atmospheric or positive pressure. The amount of solvent is not critical but a sufficient quantity should be present so that the reaction mixture can be agitated. Suitable solvents are organic solvents liquid at reaction conditions such as aliphatic hydrocarbons, ethers, and mixtures thereof.

Suitable aliphatic hydrocarbon solvents are one or more of the group consisting of hexane, heptane, octane, nonane, decane, undecane, dodecane, tridecane, pentadecane, etc. Branched chain paraffins as well as the normal paraffins are satisfactory. Suitable aromatic solvents for my reaction are one or more of the members of the group consisting of benzene, toluene, ortho-xylene, meta-xylene, p-xylene, ethylbenzene, 1, 3, 5 trimethyl benzene, various chlorinated benzenes and chlorinated xylenes. Suitable ethers are one or more members of the group consisting of diethyl ether, dipropyl ether, dibutyl ether, ethylpropyl ether, butyl propyl ether, 1,4 dioxane, anisole, ethoxybenzene, tetrahydrofuran and others. Mixtures of the aliphatic hydrocarbons, aromatic hydrocarbons and ether solvents can also be used.

Dimethyltin dichloride itself may be used as the solvent for methyl chloride. Since it is the main product of the reaction, the amount added initially is not critical. If the catalyst has a melting point below the reaction temperature, it too may serve as the solvent; however, this may require separation from the product when the reaction is completed. The preferred solvent is dimethyltin dichloride and it is normally used in an amount of about 0.05 to 1.0 mole per gram-atom of tin metal, preferably 0.2 to 0.4 mole per gram-atom of tin metal. Larger amounts of dimethyltin dichloride may be used as solvent but no additional advantage is realized.

The methyl chloride can be introduced to the reaction continuously at a rate approximately equal to its reaction with the tin metal. This type of reaction can conveniently be carried out at atmospheric pressure. If it is desired to use an autoclave the methyl chloride can be introduced continuously under pressure.

In another form of my process the tin metal, the sulfonium or isothiuronium catalyst are placed in a stirring or rocking autoclave and methyl chloride is added to the autoclave as a liquid. The entire requirement of methyl chloride can be added initially as a liquid after which the autoclave is sealed and heat applied to the autoclave to bring the temperature of the reactants in the autoclave within the range of about 120° C. to 300° C. Initially, the reaction pressure will be quite high and will gradually reduce as the methyl chloride is consumed. Initial pressures as high as 1500 psi. have been observed. At the conclusion of the reaction period any unreacted methyl chloride can be recovered by venting it to a condenser system when it can be liquified.

The best mode of practicing my invention will be apparent from a consideration of the following examples:

EXAMPLE 1

Into a 300 ml stainless steel stirred autoclave were placed 21.97 g (0.10 mole) of dimethyltin dichloride, 59.35g (0.50 mole) of granular tin (20 mesh), and 1.6g(0.026 mole) of dimethyl sulfide. Methyl chloride (66.9g, 1.32 mole) was condensed into the autoclave which was immersed in a dry ice-methanol bath. The mixture was then heated slowly to 205° C. Stirring was commenced when the temperature reached 100° C. and held at this temperature until no more methyl chloride was consumed (1½ hours). During the reaction period, the internal pressure dropped from a high of 1000 psi to 300 psi. After the autoclave cooled to room temperature, the excess of methyl chloride was vented and 134.1g (99.6% yield) of product was obtained. [The yield is based on dimethyltin dichloride expected plus dimethyltin dichloride added as solvent plus trimethyl sulfonium chloride catalyst.]

Analysis: Calcd. for total dimethyltin dichloride plus catalyst: Cl, 32.3; S, 0.62; Sn, 52.9. Found for total dimethyltin dichloride plus catalyst: Cl, 32.6; S, 0.70; Sn, 52.1.

Gas Chromatographic Analysis of the methylene chloride solubles (total product less catalyst) gives the following results:
$(CH_3)_2SnCl_2$ - 99.64
$(CH_3)_3SnCl$ - 0.36

EXAMPLE 2

Following the procedure outlined in Example 1, except that the quantities of dimethyltin dichloride (added as solvent) and dimethyl sulfide were each doubled, there was obtained 156.5g (98.2% yield) of product. The reaction time was 30 minutes during which the internal pressure dropped from 940 psi to 300 psi.

Analysis: Calcd. for total dimethyltin dichloride plus catalyst: Cl, 32.3; S, 1.01; Sn, 52.2. Found for total dimethyltin dichloride plus catalyst: Cl, 32.5; S, 1.19; Sn, 51.9.

Gas Chromatographic Analysis of the methylene chloride solubles (total product less catalyst) gave the following results:
$(CH_3)_2SnCl_2$ - 99.91%
$(CH_3)_3SnCl$ - 0.07%
Unknown - 0.02%

EXAMPLE 3

Following the procedure outlined in Example 2, except that tetrahydrothiophene (4. 4g, 0.05 mole) was used in place of dimethyl sulfide, there was obtained 157.6g (98.1%) of product calculated as total dimethyltin dichloride plus tetramethylenemethylsulfonium chloride catalyst. The reaction time was 1½ hours during which the internal pressure dropped from 900 psi to 200 psi.

Analysis: Calcd. for total dimethyltin dichloride plus catalyst: Cl, 32.0; S, 1.00; Sn, 51.7. Found for total dimethyltin dichloride plus catalyst: Cl, 31.6; S, 0.91; Sn, 52.1.

Gas Chromatographic Analysis of the methylene chloride solubles (total product less catalyst) gave the following results:
$(CH_3)_2SnCl_2$ - 98.4%
$(CH_3)_3SnCl$ - 0.4%
Unknowns - 1.3%

EXAMPLE 4

Following the procedure outlined in Example 2, except that part of the granular tin was replaced by mossy tin (about 25%) and tetramethylenemethylsulfonium iodide (5.75g, 0.025 mole) was used in place of dimethyl sulfide, there was obtained 154.9g (97.2% yield) of product. The reaction time was 45 minutes and the internal pressure dropped from 890 psi to 280 psi.

Analysis: Calcd. for total dimethyltin dichloride plus catalyst: Cl, 31.1; I, 1.99, S, 0.50; Sn, 52.1. Found for total dimethyltin dichloride plus catalyst: Cl, 31.7; I, 1.09; S, 0.77; Sn, 52.0.

Gas Chromatographic Analysis of the methylene chloride solubles (total product less catalyst) gave the following results:
$(CH_3)_2SnCl_2$ - 99.6%
Unknowns - 0.4%

EXAMPLE 5

Following the procedure outlined in Example 1, except that thiourea is used in place of dimethyl sulfide, there is obtained a mixture of dimethyltin dichloride and catalyst (S-methylisothiuronium chloride).

EXAMPLE 6

Following the procedure outlined in Examle 1, except that S-butylisothiuronium iodide is used in place of dimethyl sulfide, there is obtained a mixture of dimethyltin dichloride and catalyst.

EXAMPLE 7

Following the procedure outlined in Example 1, except that N,N,N',N'-tetramethyl-S-methylisothiuronium bromide is used in place of dimethyl sulfide, there is obtained a mixture of dimethyltin dichloride and catalyst.

EXAMPLE 8

Following the procedure outlined in Example 1, except that diethylmethylsulfonium bromide is used in place of dimethyl sulfide, there is obtained a mixture of dimethyltin dichloride and catalyst.

EXAMPLE 9

Into a 250 ml three-necked flask equipped with a stirrer, water condenser, and a gas inlet tube were charged 43.93g (0.20 mole) of dimethyltin dichloride, 23.01g (0.10 mole) of tetramethylenemethylsulfonium iodide, and 59. 35g (0.50 mole) of mossy tin. The flask was heated in an oil bath to 155°–165° C. while methyl chloride was bubbled through the mixture at atmospheric pressure at a rate approximately equal to its consumption. After 8 hours, all of the tin metal was consumed. The contents were cooled to room temperature and 162.0g (91.6% yield) of product was obtained. [The yield is based on dimethyltin dichloride expected plus dimethyltin dichloride added as solvent plus catalyst (tetramethylenemethylsulfonium iodide)].

Analysis: Calcd. for total dimethyltin dichloride plus catalyst: Cl, 28.0; I, 7.17; S, 1.82; Sn, 47.0. Found for total dimethyltin dichloride plus catalyst: Cl, 29.2; I, 3.45; S, 1.83; Sn, 45.6.

EXAMPLE 10

Following the procedure of Example 9, except that tetramethylenebutylsulfonium iodide was used in place of tetramethylenemethylsulfonium iodide, there was obtained 165.0g (91.2% yield) of product [total dimethyltin dichloride plus catalyst (tetramethylenebutylsulfonium iodide)].

Analysis: Calcd. for total dimethyltin dichloride plus catalyst: Cl, 27.4; I, 7.01; S, 1.77; Sn, 45.9.

Found the total dimethyltin dichloride plus catalyst: Cl, 28.0; I, 3.41; S, 1.83; Sn, 47.2.

Dimethyltin dichloride is used as an intermediate in the manufacture of organotin mercaptides which are used as stabilizers for halogenated resins. For example, dimethyltin dichloride will react with an organo mercaptan in the presence of an acid acceptor to form the corresponding organotin mercaptide. The use of these materials as PVC stabilizers is disclosed in "Encyclopedia of PVC", Vol. 1, Marcel Dekker Inc., N.Y.C., pages 295 to 384.

I claim:

1. The process for catalytically making dimethyltin dichloride in essentially quantitative yield by contacting tin metal with methyl chloride at a temperature within the range of about 120° C. to 300° C. for a period within the range of 0.5 to 24 hours while in the presence of a single sulfonium or isothiuronium salt catalyst selected from the group consisting of:

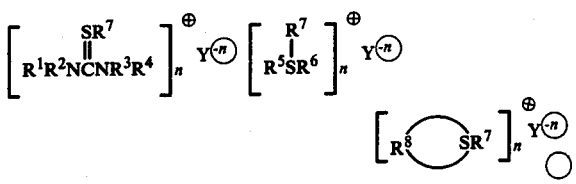

wherein:
$R^1$, $R^2$, $R^3$, $R^4$, $R^5$, $R^6$, and $R^7$ are hydrocarbyl radicals of 1 to 24 carbon atoms, $R^1$, $R^2$, $R^3$, and $R^4$ can also be hydrogen;
$R^8$ is a hydrocarbon linking group of 3-5 carbon atoms;
Y is an anion, n is the valence of anion Y; and while in the presence of a liquid solvent for methyl chloride at the beginning of the reaction.

2. The process according to claim 1 conducted at a pressure within the range of 0 to 1500 p.s.i.

3. The process according to claim 1 conducted at a temperature within the range of about 130° C. to 220° C.

4. The process according to claim 1 in which the solvent for methyl chloride is dimethyltin dichloride.

5. The process according to claim 1 in which Y is selected from the group consisting of:
$Cl^{-1}$, $Br^{-1}$, $I^{-1}$, $SnCl_3^{-1}$, $SnB_3^{-1}$, $SnI_3^{-1}$, $SnCl_5^{-1}$, $SnCl_6^{-2}$, $SnBr_5^{-1}$, $SnBr_6^{-2}$, $SnI_5^{-1}$, and $SnI_6^{-2}$.

6. The process according to claim 1 in which the sulfonium or isothiuronium salt catalyst is selected from the group consisting of:

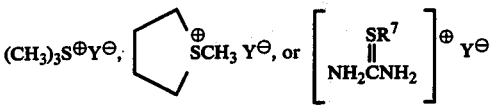

where Y is Cl, Br, or I, and $R^7$ is $CH_3$, $C_2H_5$, $C_4H_9$ or $C_6H_5CH_2$.

7. The process according to claim 1 in which the sulfonium salt catalyst is prepared in the reaction mixture by contacting methyl chloride with dimethylsulfide or tetrahydrothiophene.

8. The process according to claim 1 in which the solvent is dimethyltin dichloride.

9. The process of claim 1 in which the liquid solvent is condensed methyl chloride and the reaction pressure is superatmospheric.

10. The process of claim 1 in which the catalyst is an isothiuronium salt of the structure shown in claim 1.

11. The process of claim 5 in which Y is Cl.

12. The process of claim 1 in which the catalyst is a sulfonium salt of the structure shown in claim 1.

* * * * *

UNITED STATES PATENT OFFICE
CERTIFICATE OF CORRECTION

Patent No. 4,129,584            Dated December 12, 1978

Inventor(s) Gerald H. Reifenberg

It is certified that error appears in the above-identified patent and that said Letters Patent are hereby corrected as shown below:

IN CLAIM 5:    $SnBr_3^{-1}$ should replace $SnB_3^{-1}$

IN CLAIM 5:    $SnCl_5^{-1}$ should replace $SnCl_S^{-1}$

*Signed and Sealed this*

*Twentieth* Day of *March 1979*

[SEAL]

Attest:

RUTH C. MASON
*Attesting Officer*

DONALD W. BANNER
*Commissioner of Patents and Trademarks*